United States Patent [19]

Harris

[11] Patent Number: 4,499,288

[45] Date of Patent: Feb. 12, 1985

[54] PROCESS FOR THE PRODUCTION OF MACROCYCLIC ESTERS AND LACTONES UTILIZING DOUBLE METAL SALT CATALYSTS

[75] Inventor: Eugene G. Harris, West Chester, Ohio

[73] Assignee: National Distillers and Chemical Corporation, New York, N.Y.

[21] Appl. No.: 501,721

[22] Filed: Jun. 6, 1983

Related U.S. Application Data

[63] Continuation-in-part of Ser. No. 285,727, Jul. 22, 1981, Pat. No. 4,393,223, which is a continuation-in-part of Ser. No. 073,755, Sep. 10, 1979, abandoned.

[51] Int. Cl.$^3$ ............... C07D 313/00; C07D 313/18; C07D 321/04; C07D 321/08; C07D 321/12; C07D 321/00; C07D 323/00
[52] U.S. Cl. ..................................... 549/266; 549/267
[58] Field of Search ................................ 549/266, 267

[56] References Cited

U.S. PATENT DOCUMENTS 3,852,309 12/1974 Simmons et al. ................ 260/347.7
4,165,321 8/1979 Harris et al. ........................ 549/266
4,218,379 8/1980 Harris et al. ........................ 549/266

FOREIGN PATENT DOCUMENTS 108762 10/1963 Czechoslovakia .
47-25071 7/1972 Japan .

OTHER PUBLICATIONS

Chemical Abstracts, vol. 56, 11728e; vol. 92, 76570f; vol. 77, 126010m.

Primary Examiner—Norma S. Milestone
Attorney, Agent, or Firm—Kenneth D. Tremain; Gerald A. Baracka

[57] ABSTRACT

A process is provided for the thermal depolymerization of polyesters to produce macrocyclic compounds utilizing mixed-metal catalysts. Useful mixed-metal catalysts consist of an aluminum alkoxide or aluminum carboxylate with an alkali metal or magnesium alkoxide or carboxylate, or double metal salts thereof. High yields and enhanced rates of reaction are obtained using the mixed-metal catalysts of this invention.

20 Claims, No Drawings

PROCESS FOR THE PRODUCTION OF MACROCYCLIC ESTERS AND LACTONES UTILIZING DOUBLE METAL SALT CATALYSTS

CROSS-REFERENCE TO RELATED APPLICATIONS

This is a continuation-in-part of application Ser. No. 285,727 filed July 22, 1981 and issued on July 12, 1983 as U.S. Pat. No. 4,393,223, which is a continuation-in-part of abandoned application Ser. No. 073,755 filed Sept. 10, 1979.

BACKGROUND OF THE INVENTION

Lactones and cyclic esters are obtained by the thermal depolymerization of the corresponding linear polyesters accompanied by ring closure. For such processes, the polyester is heated at an elevated temperature in the presence of a catalyst. The reaction is carried out under reduced pressure and the macrocyclic compound and other volatile products formed during the course of the depolymerization are removed from the reaction zone as they are formed. Due to the poor heat transfer within the highly viscous reaction mass, until recently it was only possible to conduct the reaction as a batch-type operation—thus severely limiting the commercial utility of the process. With the discovery of the process of U.S. Pat. No. 4,165,321, however, the continuous and semi-continuous production of macrocyclic compounds by thermolysis of polyester is now possible.

Chlorides, nitrates, carbonates and oxides of magnesium, manganese, iron, cobalt and tin (all in the divalent state) are disclosed to be effective catalysts for the batch depolymerization of linear polyesters in U.S. Pat. No. 2,092,031. For the process of U.S. Pat. No. 4,165,321 Lewis metal salts such as the oxides, hydroxides, halides, or carboxylates, of Group IIIa, IVa, IVb, Va, VIIb and VIII metals are indicated to be useful catalysts. Yasakawa et al. reported the use of lead catalysts (oxide, hydroxide, carbonate, nitrate, borate or organic acid salts) for the preparation of large ring lactones via thermal depolymerization in Chemical Abstracts, Vol. 78 (1973), 158966q and 158968s. Cyclic esters are also obtained via thermal degradation of polyesters using $SnCl_2.2H_2O$ (Chemical Abstracts Vol. 86 (1977), 156163s) and in U.S. Pat. Nos. 4,105,672; 4,136,098; and 4,157,330 a tin carboxylate or an organotin compound in conjunction with an O,O-dialkyl-(3,5-di-t-butyl-4-hydroxy-benzyl)phosphonate is employed to catalyze the reaction. In somewhat related procedures, cyclic ester anhydrides of α-hydroxycarboxylic acids are formed in vacuo by depolymerizing the corresponding linear polymer at 200°–240° C. in the presence of lead (II) stearate (British Pat. No. 1,108,720).

While all of the aforementioned metal compounds catalyze the depolymerization and ring closure to varying extents, whether the process is conducted as a batch or continuous operation, they are not without certain disadvantages. In the first place, many of these catalysts are insoluble or have limited solubility in the reaction medium and give poor yields of the desired macrocyclic products. Even when acceptable yields are obtained the rates of reaction are often slower than desirable so that process equipment can be utilized at only a fraction of its capacity. Efforts to increase the reaction rate by raising the temperature of reaction are only partially successful since this often leads to destructive thermal decomposition and/or excessive foaming, particularly in batch-type operations.

Additionally, it is virtually impossible to completely eliminate the presence of some heavy metal contaminants in the macrocyclic product. The presence of even trace amounts of heavy metal residues can impart undesirable discoloration to the product and, if the product is stored, may promote degradation of the macrocyclic compound or other components formulated therewith. An even more serious problem exists when the catalyst is derived from a toxic metal, such as lead. Toxic metal contaminants cannot be tolerated in most applications where macrocyclic compounds are utilized and this either precludes the use of the products in these application areas or makes it necessary to subject the macrocyclic product to costly and time consuming post-treatment operation(s) capable of eliminating the metal residue.

Aluminum oxide has been used for depolymerizations carried out at atmospheric pressure using superheated steam (Czech Pat. No. 108,726) and the use of aluminum is reported in Japanese Pat. No. Sho 35(1961)-1375 for the thermal depolymerization of polyesters to form cyclic esters and lactones. Aluminum alkoxides derived from simple alcohols are used for the preparation of large-ring lactones and large-ring ethylene dioates in Japan No. 72 25,071 and Japan Kokai Tokkyo Koho No. 79,115,390, respectively.

SUMMARY OF THE INVENTION

This invention relates to an improved process whereby it is possible to obtain macrocyclic compounds, including esters, ether-esters, lactones and ether-lactones in good yield by the thermal depolymerization of polyesters utilizing mixed metal catalysts. Furthermore, it has been observed that by the use of these mixed metal catalysts rates of reaction are significantly increased and it is possible to conduct the reaction at higher temperatures than was heretofore possible. By the process of this invention it is also possible to conveniently and economically obtain macrocyclic compounds which are completely free of troublesome heavy metal residues.

For the present improved process a linear polyester is heated at a temperature in the range 200° C. to 400° C. under reduced pressure in the presence of a mixed metal catalyst comprised of an aluminum alkoxide or aluminum carboxylate and an alkoxide or carboxylate of lithium, sodium, potassium or magnesium. Typically the depolymerization is carried out at a pressure from about 10 mm Hg to 0.01 mm Hg and the catalyst is present in an amount from about 0.01 to 20 weight percent, based on the polyester. The resulting cyclic esters, cyclic ether-esters, lactones and ether-lactones will have from 8 to 20 carbon atoms.

Aluminum alkoxides useful for the invention are derived from conventional monofunctional branched- or straight-chain alcohols or alkoxyalcohols and have the formula $Al[O{-}(C_mH_{2m}){-}R_1]_3$ where m is an integer from 1 to 22 and $R_1$ is hydrogen or an alkoxy or polyalkoxy group having 1 to 16 carbons. The carboxylates of aluminum have the formula

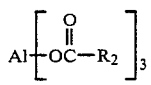

where $R_2$ is a $C_{2-22}$ alkyl (saturated or containing unsaturation), phenyl or substituted-phenyl having 7 to 20 carbon atoms.

Especially useful catalysts of this invention are mixed metal catalysts obtained when the aluminum alkoxide or aluminum carboxylate is combined with the alkali metal or magnesium alkoxide or carboxylate. The alkoxide and carboxylate moieties of the alkali metal or magnesium can be the same or different as that of the aluminum. Up to about 10 moles alkali metal or magnesium compound can be used per mole of the aluminum component, however, the molar ratio will more usually range from 0.05:1 to 8:1. Mixed metal catalysts obtained from alkoxides or carboxylates of lithium, sodium and potassium are particularly desirable.

The components of the mixed metal catalyst may be added individually to the reactor or the components can be reacted and the resulting double metal salts employed. Useful double metal salts obtained by reacting the aluminum alkoxide or carboxylate and alkali metal compound correspond to the general formula

where m, $R_1$ and $R_2$ are the same as defined above, M represents the alkali metal, a is an integer from 1 to 3, b and c are integers from 0 to 6 and $b+c=a+3$.

DETAILED DESCRIPTION

The present invention relates to an improvement in the process for the depolymerization of linear polyesters accompanied by ring closure to form macrocyclic esters and lactones having from 8 to 20 atoms in the ring, said improvement comprising the use of an aluminum alkoxide or aluminum carboxylate mixed metal catalyst.

Thermal depolymerization reactions are well known and in this regard reference may be had to the references previously referred to. Thermal depolymerization of polyesters is typically accomplished at temperatures in the range 200° C. to 400° C. and, more usually, in the range 250° C. to 360° C. Subatmospheric pressures are employed to facilitate removal of the macrocyclic products. The pressure will generally be less than about 50 mm Hg and, most preferably, will range from about 10 mm Hg to 0.01 mm Hg. The temperature and pressure employed for the reaction will vary depending on the particular polyester to be depolymerized, the manner of operation and design of the process equipment.

Polyesters useful in these depolymerization processes are obtained by conventional methods known to the art. If cyclic esters and ether-esters are to be produced the polyester will have the formula

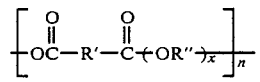

where R' represents a bivalent hydrocarbon radical of a dicarboxylic acid, R" represents a bivalent hydrocarbon radical of a diol, x is 1 in the case of cyclic esters and greater than 1 for cyclic ether-esters, and n represents the number of repeating units in the polyester, i.e., degree of polymerization. For the production of lactones and ether-lactones the polyesters will have the respective formulae

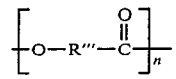

and

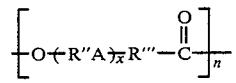

where R", x and n are the same as above, R''' represents a bivalent hydrocarbon radical and A is an oxygen or sulfur atom. The above formulae indicate the recurring units present in the linear polyester without regard to terminal groups. It is advantageous to use polyesters which are terminated with monocarboxylic acid(s) and/or monofunctional alcohol(s) to control the molecular weight and viscosity of the polymer. Polyesters having acid values and hydroxyl values less than about 20 and, more usually, less than 10 are particularly useful. The degree of polymerization of the polyesters will generally be between about 5 and 150.

The polyesters are derived from conventional dicarboxylic acids, diols and hydroxymonocarboxylic acids. Preferably these reactants are aliphatic and may be saturated or contain olefinic unsaturation and can be branched- or straight-chain. Aromatic or alicyclic dicarboxylic acids will contain from 3 up to about 18 carbon atoms and more preferably these acids will have from about 8 to 14 carbon atoms. Useful dicarboxylic acids include, for example, malonic acid, maleic acid, succinic acid, glutaric acid, adipic acid, pimelic acid, azelaic acid, sebacic acid, undecanedioic acid, dodecanedioic acid, brassylic acid, pentadecanedioic acid, and the like. Mixtures of two or more dicarboxylic acids may also be employed. Polyesters derived from alicyclic acids such as cyclohexane-1,4-dicarboxylic acid and 1,3-cyclohexadiene-1,4-dicarboxylic acid may also be used. $C_{9-13}$ saturated aliphatic dicarboxylic acids are especially preferred since macrocyclic compounds derived therefrom exhibit especially desirable fragrance properties which make them useful in a wide variety of cosmetic applications.

Hydroxymonocarboxylic acids used for the preparation of polyesters include 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, 12-thia-16-hydroxyhexadecanoic acid, and the like.

Diols from which useful polyesters are typically derived by reaction with the aforementioned dicarboxylic acids are primarily aliphatic diols having from 2 to 12, and more preferably, 2 to 6 carbon atoms. The diols are preferably saturated and can be either straight-chain or branched. Useful diols include ethylene glycol, 1,2- or 1,3-propanediol, 1,2-, 1,3-, or 1,4-butanediol, 1,6-hexanediol, 3-methyl-1,5-pentanediol, 2,3-dimethyl-2,3-butanediol, 1,8-octanediol, 2-ethylhexanediol, 1,10-decanediol, 1,12-dodecanediol, diethylene glycol, triethylene glycol, tetraethylene glycol, and the like. Alicyclic diols such as 1,4-cyclohexadimethanol may also be employed. Polyesters derived from ethylene glycol and di-, tri- and tetraethylene glycol are especially advantageous for use in depolymerization processes of this type.

Employing polyesters of the above types in the process of this invention, it is possible to obtain cyclic esters, cyclic ether-esters, lactones and ether-lactones having from 8 to 20 carbon atoms in the ring. The cyclic esters and ether-esters will have the general formula

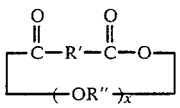

where R' is a bivalent aliphatic hydrocarbon radical, which can be branched- or straight-chain, saturated or contain unsaturation, having from 1 to 16 carbon atoms, R" is a saturated bivalent aliphatic hydrocarbon radical having 2 to 12 carbon atoms and x is an integer from 1 to 4. Especially useful cyclic esters and ether-esters are those where the moiety R' is a saturated radical having from 3 to 12 carbon atoms, the radical R" has 2 to 6 carbon atoms, and x is 1 or 2. Lactones and ether-lactones obtained by the present improved process from polyesters of the above-identified types will have the formula

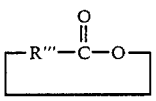

or

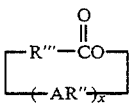

wherein R''' represents a bivalent aliphatic hydrocarbon radical having from 6 to 18 carbon atoms, R" represents a saturated bivalent aliphatic hydrocarbon radical having 2 to 12 carbon atoms, A is oxygen or sulfur, and x is an integer from 1 to 4. Preferred lactones and ether-lactones are those where R''' is a saturated bivalent aliphatic hydrocarbon radical having from 10 to 14 carbon atoms, R" contains from 2 to 6 carbon atoms, A is oxygen, and x is 1 or 2.

Illustrative macrocyclic esters and ether-esters which can be produced in accordance with the depolymerization process of this invention include: 3,6,9-tridecamethylene malonate, dodecamethylene malonate, decamethylene malonate, ethylene suberate, ethylene azelate, 3-oxa-pentamethylene azelate, 3-methylpentamethylene sebacate, ethylene undecanedioate, ethylene dodecanedioate, ethylene brassylate, ethylene-α-methylbrassylate, ethylene-α,α-dimethylbrassylate, ethylene-α-ethylbrassylate, and the like. In addition to the aforementioned products still other cyclic compounds such as tetradecamethylene carbonate, dodecamethylene oxalate and 7-oxa-tridecamethylene oxalate and bicyclic and polycyclic materials such as hexamethylene, tetra- (or hexa-) hydrophthalate can be obtained by the process of this invention. Exemplary lactones and ether-lactones corresponding to the above formulae include: pentadecanolide, 12-oxa-pentadecanolide, 12-thia-pentadecanolide, hexadecanolide, 10-oxa-hexadecanolide, 11-oxa-hexadecanolide, 11-thia-hexadecanolide and 12-oxa-hexadecanolide.

The improvement of this invention for the depolymerization of polyesters consists of the use of specific mixed metal catalysts wherein one of the metals is aluminum. Aluminum alkoxides and carboxylates are employed to obtain the mixed metal catalysts. While these aluminum compounds are effective catalysts by themselves for the thermal depolymerization and ring closure reaction, it has quite unexpectedly been discovered that improved results are obtained if an alkali metal or magnesium alkoxide or carboxylate is employed therewith or reacted with the aluminum compound to form a double metal salt. Such catalytic systems obtained from aluminum alkoxides or aluminum carboxylates with alkoxides or carboxylates of lithium, sodium, potassium or magnesium are referred to hereinafter as mixed metal or plural metal catalysts and are particularly effective depolymerization catalysts.

Rapid reaction rates and high yields of the desired macrocyclic product are obtained by the process of this invention. In addition to these advantages, the use of troublesome heavy metals is avoided by the use of the mixed metal catalysts and the process can be carried out at higher temperatures than was heretofore considered possible with minimal thermal decomposition. The amount of catalyst employed for the depolymerization reaction will generally range from about 0.01 to about 20 percent by weight, based on the polyester. While even larger quantities of catalyst can be utilized, any advantage realized thereby is generally offset by the additional cost involved. Most usually the mixed metal catalyst will be present in an amount from 0.1 to 10 weight percent.

Aluminum alkoxides and carboxylates used to obtain the mixed metal catalysts of this invention have the respective formulae

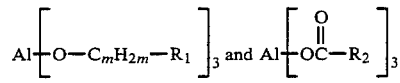

where m is an integer from 1 to 22, $R_1$ is hydrogen, an alkoxy or polyalkoxy radical having from 1 to 16 carbon atoms, and $R_2$ is an alkyl group having from 2 to 22 carbon atoms and which can be saturated or contain unsaturation, phenyl or substituted-phenyl having from 7 to 20 carbon atoms. Especially useful alkoxides and carboxylates are those wherein m is an integer from 2 to 12 and $R_1$ is hydrogen, methoxy, ethoxy or di-, tri-, or tetraethoxy, and wherein $R_2$ is a $C_{8-18}$ alkyl group, phenyl, or a substituted phenyl wherein the substituent is an alkyl, alkoxy or polyalkoxy group. The alkoxides and carboxylates of aluminum may be employed individually or a mixture of two or more of these compounds can be used. Furthermore, these compounds may be added to the reactor as such or generated in the reaction environment. For example, the aluminum may be introduced as an enolate, such as isopropoxy aluminum acetoacetonate, and the chelating group displaced by alkoxide and/or carboxylate groups.

While the above-defined aluminum alkoxides and aluminum carboxylates are useful catalysts for the thermal depolymerization of polyesters to produce macrocyclic compounds, it has quite unexpectedly been discovered that catalytic activity is significantly enhanced if an amount ranging up to about 10 moles of an alkali metal or magnesium alkoxide or carboxylate is present per mole aluminum compound. Highly effective mixed metal catalysts capable of giving very rapid rates of depolymerization are obtained when from 0.05 to 8 moles alkali metal or magnesium compound is present per mole aluminum compound. Especially useful catalysts are those wherein from about 0.1 to 3 moles of a carboxylate or alkoxide of lithium, sodium or potassium is present per mole aluminum alkoxide or carboxylate.

Useful alkoxides and carboxylates of alkali metals or magnesium will be of the same type as described above for the aluminum compounds. In other words these compounds will correspond to the formulae

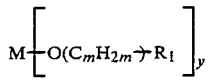

or

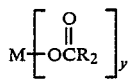

where M is lithium, sodium, potassium or magnesium, y is 1 when M is lithium, sodium or potassium and 2 when M is magnesium and m, $R_1$ and $R_2$ are the same as defined above.

It is not necessary for the present mixed metal catalysts that both metals contain the same alkoxide or carboxylate moieties. For example, if aluminum and alkali metal carboxylates are employed they can be derived from different carboxylic acids. It is also possible and sometimes advantageous to employ an alkali metal alkoxide with an aluminum carboxylate or, conversely, an aluminum alkoxide can be used with an alkali metal carboxylate.

Especially useful alkoxides for the mixed metal catalysts of this invention are derived from conventional $C_{1-8}$ aliphatic monofunctional branched- or straight-chain alcohols or from a $C_{3-12}$ alkoxyalcohol, such as monomethylethylene glycol, monoethylethylene glycol, ethoxydiethylene glycol, ethoxytriethylene glycol, methoxypolyethylene glycols, ethoxypolyethylene glycols and the like. Similarly, the carboxylates of the aluminum, alkali metal or magnesium are typically derived from the same or different branched- or straight-chain aliphatic (fatty) acids which can contain olefinic unsaturation, benzoic acid or $C_{1-8}$ alkyl substituted benzoic acid.

The mixed metal catalyst is obtained by combining the above-described aluminum compound(s) and lithium, sodium, potassium or magnesium compound(s) in the prescribed molar proportions. This can be accomplished by adding the aluminum compound and alkali metal or magnesium compound to the reactor as such or these compounds can be reacted prior to addition to the polymerization vessel to form double metal salts. When the components of the mixed metal catalyst are combined prior to introduction into the reactor, the components may be physically admixed or, depending on the particular components and the conditions employed, partially or completely reacted. This is accomplished with agitation, preferably under a nitrogen atmosphere, and in the absence of moisture. Where the catalyst components are reacted prior to introduction to the reactor, the resulting mixed metal salt, which is also an effective depolymerization catalyst for the process, will vary in its composition depending on the nature and molar ratio of the components and the conditions employed. In some instances, such as where an alkoxide of aluminum is reacted with an alkali metal carboxylate, the resulting double metal salt may have entirely different physical and chemical characteristics than either of the components. For example, both metal components may be solids whereas the resulting mixed metal salt obtained upon heating will be a liquid. This feature can be advantageous in that it facilitates handling and introduction of the catalyst to the depolymerization reactor. The ultraviolet spectra and absorbtivity of the mixed metal reaction products differ from what one would obtain from a simple mixture of the reactants. The double metal salts obtained by reacting the aluminum carboxylate or alkoxide with the alkali metal alkoxide or carboxylate correspond to the general formula Al $M_a(OC_mH_{2m}R_1)_b(OOCR_2)_c$ where m, $R_1$ and $R_2$ are the same as identified above, M represents the alkali metal, a is an integer from 1 to 3, b and c are integers from 0 to 6 and $b+c=a+3$. In an especially useful embodiment a is equal to 1 or 3.

Particularly advantageous results are obtained using double metal salts obtained by reacting essentially equimolar amounts of the aluminum compound and alkali metal compound. Such mixed metal salts have the formula Al M $(OC_mH_{2m}R_1)_d$ $(OOCR_2)_e$ where M is lithium, sodium or potassium, d and e are integers from 0 to 4, and $d+e=4$. Especially useful mixed metal salts are obtained when M is sodium or potassium and $d=3$, $e=1$ or $d=4$, $e=0$.

The manner in which the depolymerization is carried out, i.e., whether the process is conducted as a batch, continuous or semi-continuous operation, will influence the amount and type of mixed metal catalyst used and the reaction conditions employed for the process. As has already been indicated the depolymerization can be carried out in conventional process equipment adaptable to removal of the macrocyclic products formed during the course of the reaction by vacuum distillation or in equipment such as that described in U.S. Pat. No. 4,165,321, capable of continuous or semi-continuous operation. If the process is conducted in accordance with the latter procedure and the mixed metal catalyst is added continuously or incrementally throughout the course of the depolymerization.

The macrocyclic compounds obtained in accordance with the present improved process are primarily useful in cosmetic applications. They impart desirable fragrance properties and/or enhance the fragrance characteristics of other compounds combined therewith. For example, the cyclic esters and ether-esters, lactones and ether-lactones have utility in detergents (heavy duty and regular laundry), soaps (bar soaps, dish soaps and specialty beauty soaps), fabric softeners, paper products, personal care products (bath oils, shampoos, hair rinses, deodorants, shaving creams and mouthwashes), and as fine fragrance components for perfumes, perfume oils, perfume fixatives, colognes, aftershave lotions and the like. Products obtained by the present improved process are particularly adaptable to applications where heavy metal residues cannot be tolerated.

The following examples illustrate the invention more fully but are not intended to limit the scope thereof. In these examples, all parts and percentages are on a weight basis unless otherwise indicated.

EXAMPLE I

Preparation of Polyester: Poly(ethylene brassylate) was prepared by charging to a top-agitated resin kettle fitted with a distillation head and condenser 109 parts dimethyl brassylate and 30.5 parts polymer grade ethylene glycol. About 2.3 percent, based on the dimethyl brassylate, methyl esters of a mixture of $C_{16-22}$ fatty acids was included as the chain terminator. A supported titanium catalyst (0.08 part), prepared from tetraisopropyl titanate and a naturally acidic montmorillonite clay in accordance with the teaching of U.S. Pat. No. 4,032,550, was then added to the reaction mixture under a positive pressure of nitrogen and heating begun. When the temperature of the reaction mixture reached about 180° C. methanol began distilling from the reaction mixture and was collected. After most of the methanol was removed and the temperature increased to about 195° C.–205° C., a vacuum of 2 in. Hg was applied and increased slowly to 30 in. Hg. Samples were periodically removed from the reactor for analysis and after about 11 hours the reaction mixture had an acid value of 0.1 and hydroxyl value of 15.3. Heating was terminated at this point, the reaction mixture cooled to about 180° C. and the vacuum broken with nitrogen. The high molecular weight poly(ethylene brassylate), viscosity 117 centistokes at 210° C., was filtered to remove the supported titanium catalyst.

A double metal salt was prepared by heating 75 parts aluminum isopropoxide (melting point 115.5° C.), 115 parts potassium stearate (melting point >260° C.), and 160 parts diethylene glycol monoethylether at 185° C. until essentially all of the isopropyl alcohol was distilled from the reaction mixture. The resulting double metal salt $KAl(OC_2H_4OC_2H_4OC_2H_5)_3(OOC_{17}H_{35})$ was a homogeneous waxy solid melting over the range 85° C.–95° C. Elemental analysis of the product confirmed the presence of 5.3 percent potassium and 3.6 percent aluminum. The double metal salt was also prepared by the reaction of essentially equal molar amounts of tri(ethoxyethoxyethyl) aluminate and potassium stearate.

Following the procedure of U.S. Pat. No. 4,165,321, poly(ethylene brassylate) was depolymerized utilizing the double metal salt as the catalyst. For the depolymerization, 1.36 weight percent $KAl(OC_2H_4OC_2H_4OC_2H_5)_3(OOCC_{17}H_{35})$ was dissolved in the polyester and the mixture transferred to a stainless steel holding tank maintained at 150° C. with agitation. From this tank the polyester was continuously metered into an electrically heated stainless steel inverted vertical cone reactor fitted with two conical, helicoidal blades whose axes coincide with the cone axes of the bowl and which intermesh as they rotate in opposite directions to provide top-to-bottom mixing throughout the total volume of the reaction mixture. The blades were positioned within the reactor so that the maximum blade-to-wall clearance (distance between the blades and the interior surface of the reactor) was about 0.25″ and driven with a high torque motor at about 20 rpm. The reaction temperature was maintained between 330° C. and 360° C. at a vacuum of about 1–5 mm Hg. Ethylene brassylate was continuously distilled from the reactor and the rate of addition of the polyester containing the mixed metal catalyst adjusted as necessary to maintain the proper material balance. The yield of crude ethylene brassylate produced in this manner was 83.6 percent.

EXAMPLE II

To demonstrate the versatility of the present process, poly(ethylene brassylate) was depolymerized in accordance with the procedure described in U.S. Pat. No. 2,092,031. Seventy-five grams of the polyester and 2 grams (2.66 weight percent) of the double metal salt of Example I were charged to a glass reaction vessel equipped with a take-off condenser. The mixture was heated to 200° C. with agitation until the mixed metal catalyst was thoroughly blended into the polymer. The reaction temperature was then increased and maintained at 320° C. at a pressure of 0.1–0.5 mm Hg. After the vapor temperature and distillate take-off stabilized, the distillate rate was recorded. Crude ethylene brassylate was obtained at a rate of 40 mls/hour (measured during the first hour). After about 2 hours the reaction was essentially complete as evidenced by a sharp reduction in the distillation rate, however, heating was continued for two additional hours to insure completion of the distillation. The yield of ethylene brassylate (crude) was 89.7 percent.

EXAMPLE III

To demonstrate the improved yields and increased reaction rates obtained utilizing the mixed metal catalysts of this invention, batch polymerizations were identically conducted using (a) a mixed metal catalyst comprised of aluminum stearate and sodium stearate (1.1 molar ratio), (b) aluminum stearate catalyst, and (c) lead stearate catalyst. These reactions were conducted in accordance with the procedure employed in Example II utilizing 74 grams poly(ethylene brassylate) and 0.5 mole percent of the catalyst. Reactions were carried out at 310°–320° C. and 0.1–0.5 mm Hg for four hours. The amount of distillate (crude ethylene brassylate) recovered was recorded after the first hour of reaction. With the mixed metal catalyst, 45 mls ethylene brassylate was obtained after one hour and the overall yield was 95.9 percent. With the aluminum stearate, 36 mls crude ethylene brassylate was obtained in the first hour and the overall yield was only 78 percent. Using lead stearate only 25 mls distillate was obtained after one hour and the yield of crude ethylene brassylate was 69.1 percent.

EXAMPLE IV

A mixed metal catalyst comprised of aluminum stearate and lithium stearate (molar ratio 1:1) was used for the depolymerization. For the reaction aluminum stearate (1.09 gram) and lithium stearate (0.36 gram) were blended in 70 grams poly(ethylene brassylate) at 200° C. The temperature was then raised to 314° C. while maintaining a vacuum of 0.05–0.1 mm Hg. Ethylene brassylate was obtained (40 mls during the first hour) in an 88.9 percent yield. Of the ethylene brassylate recovered, 90 percent of the product was obtained after 2 hours.

EXAMPLE V

A mixed metal catalyst comprised of 0.40 gram potassium stearate and 1.09 gram aluminum stearate (molar ratio 1:1) was employed at a 2.1 weight percent level to depolymerize poly(ethylene brassylate) at a temperature of 316° C. and pressure of 0.10–0.15 mm Hg. 88.7 Percent yield crude ethylene brassylate containing less than 3 ppm aluminum and only 1.2 ppm potassium was obtained. In a similar manner, ethylene brassylate was produced using the same level of a mixed metal catalyst comprised of 0.74 gram magnesium stearate and 1.09 gram aluminum stearate.

EXAMPLE VI

Mixed metal catalysts comprised of potassium stearate and aluminum stearate were utilized to depolymerize poly(ethylene brassylate). The molar ratios of catalyst components were varied from 3:1 to 1:10 (potassium stearate:aluminum stearate). Reaction conditions and percent yield ethylene brassylate are provided below for each of the catalysts.

| K Stearate: Al Stearate (mole ratio) | Wt. % Catalyst | Reaction Temp. (°C.) | Reaction Press. (mm Hg) | % Yield |
|---|---|---|---|---|
| 3:1 | 3.3 | 320 | 0.5 | 89.7 |
| 3:1 | 6.6 | 316 | 0.2 | 78.1 |
| 1:3 | 1.7 | 314 | 0.3 | 82.2 |
| 1:10 | 14.5 | 320 | 1.5 | 70 |

Excellent rates of reaction based on distillation data obtained during the first hour of reaction were observed for all of the above-reactions.

EXAMPLE VII

Aluminum tripelargonate, obtained by reacting 0.5 mole aluminum isopropoxide and 1.5 mole pelargonic acid at 120° C., was combined with an equimolar amount, based on aluminum, of potassium stearate and the resulting mixed metal catalyst (1.7 weight percent) charged to a reactor with 76 grams poly(ethylene brassylate). The depolymerization was conducted in the usual manner. Ethylene brassylate was obtained at a rate of 42 mls/hour and yield of 89.3 percent.

EXAMPLE VIII

A mixed metal catalyst comprised of potassium brassylate and aluminum stearate (1:1 molar ratio of K:Al) was employed for the depolymerization of poly(ethylene brassylate) at a 1.8 weight percent level. An 81.6 percent yield of ethylene brassylate was obtained. Comparable yields are obtained when this mixed metal catalyst is used for the depolymerization of poly(ethylene sebacate) and poly(3-oxa-pentamethylene azelate).

EXAMPLE IX

Sodium brassylate (0.33 gram) and aluminum stearate (1.09 gram) were added to 70 grams poly(ethylene brassylate) and the mixture heated at 200° C. until a homogeneous viscous mass was obtained. The molar ratio of sodium to aluminum was 2:1. The temperature was then increased to 312° C. and the pressure reduced to 0.3–0.5 mm Hg. The depolymerization reaction was complete in about 3 hours and 88.1 percent yield ethylene brassylate was obtained.

EXAMPLE X

A mixed metal catalyst was prepared by heating 0.05 mole powdered aluminum isopropylate (melting point 118° C.), 0.05 mole potassium stearate and 0.15 mole ethyl cellusolve ($HOC_2H_4OC_2H_5$) at 140° C. while removing the theoretical amount of isopropanol. Five-tenths mole percent of the resulting high melting (melting point >200° C.) double metal salt $AlK(OC_2H_4OC_2H_5)_3(OOCC_{17}H_{35})$ was used to catalyze the depolymerization of an acid-terminated poly(ethylene brassylate) (AV<10; OHV<10) at 320° C. and 0.1 to 0.5 mm Hg. Forty-two mls crude ethylene brassylate was distilled from the reaction vessel during the first hour and the overall yield of the ethylene brassylate was 82.4 percent.

EXAMPLE XI

Repeating Example X, a double metal salt was prepared except that sodium stearate was substituted for the potassium stearate and the ethyl cellusolve was replaced with diethylene glycol monoethyl ether. The resulting double metal salt $NaAl(OC_2H_4OC_2H_4OC_2H_5)_3(OOCC_{17}H_{35})$ was used as the catalyst for the continuous depolymerization of poly(ethylene brassylate) in accordance with the procedure and conditions of Example I. Ethylene brassylate was continuously produced and distilled from the reactor at a rapid rate and the overall yield was 73.2 percent. Comparable results are obtained using the double metal salt $NaAl(OC_2H_4OC_2H_5)_3(OOCC_6H_5)$ obtained by the reaction of sodium benzoate and aluminum tricellusolve ($Al(OC_2H_4OC_2H_5)_3$).

EXAMPLE XII

A mixed metal compound of the formula $NaAl(OCH_2CH_2OCH_3)_2(O(CH_2)_6CH_3)_2$, and identical to that obtained by combining sodium heptoxide with heptyl di(methoxyethyl) aluminate, was prepared by adding 0.25 mole sodium bis-2-methoxyethoxy aluminum hydride (70% solution in benzene) to 0.5 mole heptanal with cooling over a two hour period. The double metal salt $NaAl(OC_2H_4OC_2H_5)_3(OOCC_6H_5)$, was recovered as a viscous liquid by evaporation of the solvent. 0.46 Grams of the mixed sodium-aluminum alkoxide catalyst was employed to depolymerize 70 grams poly(ethylene brassylate) at 310°–314° C. and 0.15–0.3 mm Hg. About 85 percent yield was obtained in two hours. Useful mixed metal alkoxide catalysts are also prepared following the procedure described in U.S. Pat. No. 3,852,309.

EXAMPLE XIII

A mixed metal catalyst comprised of aluminum isopropoxide and sodium methoxide (1:1 molar ratio) was utilized to depolymerize poly(ethylene brassylate). The mixed metal catalyst was employed at a 0.48 weight percent level. Ethylene brassylate was obtained at a rate of 44.5 mls per hour (based on the amount collected during the first hour of the reaction) and the overall yield at the end of the four hours was 80 percent.

EXAMPLE XIV

The ability to depolymerize different polyester compositions to obtain a variety of useful macrocyclic compounds is demonstrated by this example wherein a mixed metal catalyst was employed for the preparation of ethylene dodecanedioate. For this reaction the catalyst was a double metal salt $KAl(OC_2H_4OC_2H_4OC_2H_5)_3(OOCC_{17}H_{35})$ (melting point 85° C.–95° C.; 5.3 percent K, 3.6 percent Al) obtained by heating equimolar amounts of aluminum tricarbitol ($Al(OCH_2CH_2OCH_2CH_2OC_2H_5)_3$) and potassium stearate. The catalyst was used at a 1.3 weight percent level in 70 grams poly(ethylene dodecanedioate). The mixture was heated to 325° C. under reduced pressure (1 mm Hg). About 75 percent conversion of the polyester to cyclic product was achieved in one hour. Eighty-six percent yield ethylene dodecanedioate was achieved. Comparable results are obtained using a polyester derived from diethylene glycol.

EXAMPLE XV

To 50 grams of the polyester of 15-hydroxypentadecanoic acid was added 2.0 grams of the mixed metal catalyst of Example XIV KAl(OC$_2$H$_4$OC$_2$H$_4$OC$_2$H$_5$)$_3$(OOCC$_{17}$H$_{35}$) and the mixture heated to 320° C. at 0.8–1.0 mm Hg. Heating was terminated after four hours during which time 43.85 grams pentadecanolide (87.7 percent yield) was obtained. An ether-lactone is produced when a polyester prepared from 12-oxa-15-hydroxypentadecanoic acid is depolymerized in a similar manner.

EXAMPLE XVI

An alcohol terminated polyester of low acid and hydroxyl value was obtained by reacting dimethyl brassylate, ethylene glycol and cetyl alcohol (0.04 mole per mole dimethyl brassylate). Seventy grams of the resulting polyester was combined with the double metal salt of Example XIV (1.36 weight percent) and the mixture heated under reduced pressure to effect depolymerization and formation of the cyclic diester product. Depolymerization proceeded at a rapid rate with no difficulty and 52.9 grams ethylene brassylate was recovered. In an identical manner, a polyester terminated with an aromatic monocarboxylic acid (p-decyloxybenzoic acid) was depolymerized and 53.7 grams ethylene brassylate obtained.

EXAMPLE XVII

NaAl(OCHCH$_3$CH$_2$CH$_3$)$_4$ was prepared by refluxing 24.7 grams aluminum tri-sec-butoxide (liquid at 25° C.), 5.4 grams sodium methoxide (melting point >300° C.) and 20 grams sec-butyl alcohol while removing methanol via a fractionating column. When the theoretical amount of methanol was removed, the temperature was raised to remove excess sec-butyl alcohol and recover the NaAl(OCHCH$_3$CH$_2$CH$_3$)$_4$ (melting point >260° C.; 6.7 percent Na; 7.9 percent Al). A vacuum was applied to the system during the final stages of the alcohol removal. The double metal salt was used for the depolymerization of poly(ethylene brassylate) in accordance with the procedure of Example I. While some of the catalyst remained undissolved in the polyester, elemental analysis of both the undissolved catalyst and soluble catalyst (recovered from the polyester) were identical. A high yield of ethylene brassylate was obtained while maintaining a good reaction rate.

EXAMPLE XVIII

The double metal salt NaAl(OC$_2$H$_4$OCH$_3$)$_4$ was prepared following the procedure of Example XVII by reacting 24.7 grams aluminum tri-sec-butoxide, 5.4 grams sodium methoxide and 30 grams methyl cellusolve. The double metal salt had a melting point >260° C., contained 6.6 percent Na and 7.7 percent Al, and was an effective catalyst for the depolymerization of poly(ethylene brassylate). The double metal salt was also obtained by reacting sodium 2-methoxyethoxide (melting point >250° C.) with aluminum tri(2-methoxyethoxide), a viscous oil at 25° C.

EXAMPLE XIX

In accordance with the general procedure described above, a double metal salt was prepared by heating 20.5 grams aluminum isopropylate, 16.2 grams sodium methoxide and 70 grams sec-butyl alcohol. During the heating, methanol, isopropanol and excess sec-butyl alcohol were consecutively removed from the reaction mixture as the temperature was increased. A vacuum was applied during the final stripping stages. The double metal salt AlNa$_3$(OCHCH$_3$CH$_2$CH$_3$)$_6$ was a waxy solid melting at 50°–60° C., contained 12.9 percent Na and 5.1 percent Al, and was an effective catalyst for the depolymerization of poly(ethylene brassylate).

EXAMPLE XX

An effective mixed metal depolymerization catalyst was obtained by reacting 24.7 grams aluminum tri-sec-butoxide, 32.3 grams potassium stearate and 100 grams propionic acid. The reaction mixture was heated while removing sec-butyl alcohol and sec-butyl propionate formed in the reaction mixture. Finally, the excess propionic acid was stripped under vacuum to obtain the KAl(OOCC$_{17}$H$_{35}$)(OOCC$_2$H$_5$)$_3$ salt (melting point >300° C.; 14.0 percent K, 9.4 percent Al). The double metal salt was employed at 0.55 weight percent level for the depolymerization of poly(ethylene brassylate) in accordance with the procedure of Example I and ethylene brassylate was obtained in good yield.

I claim:

1. A process for the production of macrocyclic compounds having 8 to 20 carbon atoms in the ring and selected from the group consisting of

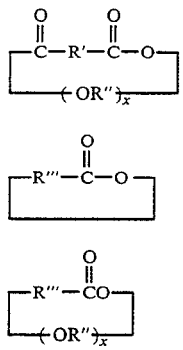

where R' is a bivalent aliphatic hydrocarbon radical having 1 to 16 carbon atoms, R'' is a saturated bivalent aliphatic hydrocarbon radical having from 2 to 12 carbon atoms, R''' is a bivalent aliphatic hydrocarbon radical having from 6 to 18 carbon atoms and x is an integer from 1 to 4, by thermal depolymerization of the corresponding linear polyester which comprises heating the polyester at a temperature from 200° C. to 400° C. and pressure less than 50 mm Hg in the presence of 0.01 percent to 20 percent by weight, based on the polyester, of a double metal salt of the formula

where M is lithium, sodium or potassium, R$_1$ is hydrogen or an alkoxy or polyalkoxy radical having from 1 to 16 carbon atoms, R$_2$ is a C$_{2-22}$ alkyl, phenyl or substituted-phenyl having 7 to 20 carbon atoms, m is an integer from 1 to 22, a is an integer from 1 to 3, b and c are integers from 0 to 6 and b+c=a+3.

2. The process of claim 1 where a is equal to 1.

3. The process of claim 2 wherein m is an integer from 2 to 12, R$_1$ is hydrogen, methoxy, ethoxy, di-, tri- or tetra-ethoxy, R$_2$ is a C$_{8-18}$ alkyl, phenyl or substituted-phenyl wherein the substituent is an alkyl, alkoxy or polyalkoxy group.

4. The process of claim 4 where the double metal salt is present in an amount from 0.1 to 10 weight percent, based on the weight of the polyester, and corresponds to the formula AlM(OC$_m$H$_{2m}$R$_1$)$_d$(OOCR$_2$)$_e$ where M is sodium or potassium, d and e are integers from 0 to 4 and d+e=4.

5. The process of claim 4 where d=3 and e=1.

6. The process of claim 5 wherein the depolymerization is carried out at a temperature in the range 250° C. to 360° C. and pressure of 10 mm Hg to 0.01 mm Hg.

7. The process of claim 6 wherein the depolymerization is conducted as a continuous or semi-continuous operation.

8. The process of claim 7 wherein the macrocyclic compound is ethylene brassylate.

9. The process of claim 7 wherein the macrocyclic compound is pentadecanolide.

10. The process of claim 4 where d=4 and e=0.

11. The process of claim 10 wherein the depolymerization is carried out at a temperature in the range 250° C. to 360° C. and pressure of 10 mm Hg to 0.01 mm Hg.

12. The process of claim 11 wherein the depolymerization is conducted as a continuous or semi-continuous operation.

13. The process of claim 12 wherein the macrocyclic compound is ethylene brassylate.

14. The process of claim 12 wherein the macrocyclic compound is pentadecanolide.

15. The process of claim 1 where a is equal to 3.

16. The process of claim 15 wherein m is an integer from 2 to 12, R$_1$ is hydrogen, methoxy, ethoxy, di-, tri- or tetra-ethoxy, R$_2$ is a C$_{8-18}$ alkyl, phenyl or substituted-phenyl wherein the substituent is an alkyl, alkoxy or polyalkoxy group.

17. The process of claim 16 wherein the double metal salt is present in an amount from 0.1 to 10 weight percent, based on the weight of the polyester, and the depolymerization is carried out at a temperature in the range 250° C. to 360° C. and pressure of 10 mm Hg to 0.01 mm Hg.

18. The process of claim 17 wherein the depolymerization is conducted as a continuous or semi-continuous operation.

19. The process of claim 18 wherein the macrocyclic compound is ethylene brassylate.

20. The process of claim 18 wherein the macrocyclic compound is pentadecanolide.

* * * * *